United States Patent [19]
Murphy et al.

[11] Patent Number: 5,607,846
[45] Date of Patent: Mar. 4, 1997

[54] VACCINE FOR MORAXELLA CATARRHALIS

[75] Inventors: Timothy F. Murphy, East Amherst, N.Y.; Reva Bhushan, North Potomac, Md.

[73] Assignee: Research Foundation of State University of New York, Amherst, N.Y.

[21] Appl. No.: 245,758

[22] Filed: May 17, 1994

[51] Int. Cl.⁶ .......................... C12P 21/02; C07H 21/04; C12N 1/21; C12N 15/63
[52] U.S. Cl. ................. 435/69.3; 435/252.3; 435/252.8; 435/320.1; 536/23.1
[58] Field of Search ................................. 435/69.1, 69.3, 435/71.2, 172.3, 320.1; 536/23.7; 935/23

[56] References Cited

PUBLICATIONS

Sambrook et al. (1989) Molecular Cloning: A Laboratory Manual (Cold Spring Harbor Press, Cold Spring Harbor).
Murphy et al., "Surface–Exposed and Antigenically Conserved Determinants of Outer Membrane Proteins of *Branhamella catarrhalis*",Infection and Immunity, vol. 57, No. 10, Oct. 1989, pp. 2938–2941.

*Primary Examiner*—David Guzo
*Assistant Examiner*—Robert Schwartzman
*Attorney, Agent, or Firm*—Hodgson, Russ, Andrews, Woods & Goodyear

[57] ABSTRACT

Compositions comprising outer membrane protein "E", and peptides and oligopeptides thereof, of *Moraxella catarrhalis* are described. Additionally, nucleotide sequences encoding the protein, peptide, or oligopeptide are disclosed, as well as recombinant vectors containing these sequences. Protein, peptide, or oligopeptide can be produced from host cell systems containing these recombinant vectors. Peptides and oligopeptides can also be chemically synthesized. Disclosed are the uses of the protein, peptides and oligopeptides as antigens for vaccine formulations, and as antigens in diagnostic immunoassays. The nucleotide sequences are useful for constructing vectors for use as vaccines for insertions into attenuated bacteria in constructing a recombinant bacterial vaccine and for inserting into a viral vector in constructing a recombinant viral vaccine. Also described is the use of nucleotide sequences related to the gene encoding E as primers and/or probes in molecular diagnostic assays for the detection of *M. catarrhalis*.

8 Claims, 2 Drawing Sheets

SEQUENCE LISTING ( 1 ) GENERAL INFORMATION:

( i i i ) NUMBER OF SEQUENCES: 18

( 2 ) INFORMATION FOR SEQ ID NO:1 :

( i ) SEQUENCE CHARACTERISTICS:
        ( A ) LENGTH: 20 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: Moraxella catarrhalis
    ( B ) STRAIN: 25240
    ( C ) CELL TYPE: bacterium ( v ) SEQUENCE DESCRIPTION: SEQ ID NO:1 :

CAAGATGGTA CATATGCGAA     20

( 2 ) INFORMATION FOR SEQ ID NO:2 :

( i ) SEQUENCE CHARACTERISTICS:
    ( A ) LENGTH: 20 nucleotides
    ( B ) TYPE: nucleic acid
    ( C ) STRANDEDNESS: single- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: Moraxella catarrhalis
    ( B ) STRAIN: 25240
    ( C ) CELL TYPE: bacterium ( v ) SEQUENCE DESCRIPTION: SEQ ID NO:2 :

CAAGATGGTA CGTATGCGAA     20

( 2 ) INFORMATION FOR SEQ ID NO:3 :

( i ) SEQUENCE CHARACTERISTICS:
    ( A ) LENGTH: 20 nucleotides
    ( B ) TYPE: nucleic acid
    ( C ) STRANDEDNESS: single- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: Moraxella catarrhalis
    ( B ) STRAIN: 25240
    ( C ) CELL TYPE: bacterium ( v ) SEQUENCE DESCRIPTION: SEQ ID NO:3 :

CAAGATGGTA CTTATGCGAA     20

( 2 ) INFORMATION FOR SEQ ID NO:4 :

( i ) SEQUENCE CHARACTERISTICS:
    ( A ) LENGTH: 20 nucleotides
    ( B ) TYPE: nucleic acid
    ( C ) STRANDEDNESS: single- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: Moraxella catarrhalis
    ( B ) STRAIN: 25240
    ( C ) CELL TYPE: bacterium ( v ) SEQUENCE DESCRIPTION: SEQ ID NO:4 :

CAAGATGGTA CCTATGCGAA     20

( 2 ) INFORMATION FOR SEQ ID NO:5 :

( i ) SEQUENCE CHARACTERISTICS:
    ( A ) LENGTH: 20 nucleotides
    ( B ) TYPE: nucleic acid
    ( C ) STRANDEDNESS: single- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: Moraxella catarrhalis
    ( B ) STRAIN: 25240
    ( C ) CELL TYPE: bacterium ( v ) SEQUENCE DESCRIPTION: SEQ ID NO:5 :

CAAGATGGCA CATATGCGAA  20

( 2 ) INFORMATION FOR SEQ ID NO:6 :

( i ) SEQUENCE CHARACTERISTICS:
    ( A ) LENGTH: 20 nucleotides
    ( B ) TYPE: nucleic acid
    ( C ) STRANDEDNESS: single- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: Moraxella catarrhalis
    ( B ) STRAIN: 25240
    ( C ) CELL TYPE: bacterium ( v ) SEQUENCE DESCRIPTION: SEQ ID NO:6 :

CAAGATGGCA CGTATGCGAA  20

( 2 ) INFORMATION FOR SEQ ID NO:7 :

( i ) SEQUENCE CHARACTERISTICS:
    ( A ) LENGTH: 20 nucleotides
    ( B ) TYPE: nucleic acid
    ( C ) STRANDEDNESS: single- stranded
    ( D ) TOPOLOGY: linear ( i i ) MOLECULE TYPE: DNA ( i i i ) IMMEDIATE SOURCE: synthesized ( i v ) ORIGINAL SOURCE:
    ( A ) ORGANISM: Moraxella catarrhalis
    ( B ) STRAIN: 25240
    ( C ) CELL TYPE: bacterium ( v ) SEQUENCE DESCRIPTION: SEQ ID NO:7 :

CAAGATGGCA CTTATGCGAA  20

( 2 ) INFORMATION FOR SEQ ID NO:8 :

( i ) SEQUENCE CHARACTERISTICS:
    ( A ) LENGTH: 20 nucleotides
    ( B ) TYPE: nucleic acid
    ( C ) STRANDEDNESS: single- stranded
    ( D ) TOPOLOGY: linear ( i i ) MOLECULE TYPE: DNA ( i i i ) IMMEDIATE SOURCE: synthesized ( i v ) ORIGINAL SOURCE:

( A ) ORGANISM: Moraxella catarrhalis
                ( B ) STRAIN: 25240
                ( C ) CELL TYPE: bacterium ( v ) SEQUENCE DESCRIPTION: SEQ ID NO:8 :

CAAGATGGCA CCTATGCGAA                                                                           20

( 2 ) INFORMATION FOR SEQ ID NO:9 :

( i ) SEQUENCE CHARACTERISTICS:
                ( A ) LENGTH: 28 nucleotides
                ( B ) TYPE: nucleic acid
                ( C ) STRANDEDNESS: single- stranded
                ( D ) TOPOLOGY: linear ( i i ) MOLECULE TYPE: DNA ( i i i ) IMMEDIATE SOURCE: synthesized ( i v ) ORIGINAL SOURCE:
                ( A ) ORGANISM: Moraxella catarrhalis
                ( B ) STRAIN: 25240
                ( C ) CELL TYPE: bacterium ( v ) SEQUENCE DESCRIPTION: SEQ ID NO:9 :

GGCTTGGGCA ACTTTGTCAT CACCCTCC                                                                  28

( 2 ) INFORMATION FOR SEQ ID NO:10 :

( i ) SEQUENCE CHARACTERISTICS:
                ( A ) LENGTH: 30 nucleotides
                ( B ) TYPE: nucleic acid
                ( C ) STRANDEDNESS: single- stranded
                ( D ) TOPOLOGY: linear ( i i ) MOLECULE TYPE: DNA ( i i i ) IMMEDIATE SOURCE: synthesized ( i v ) ORIGINAL SOURCE:
                ( A ) ORGANISM: Moraxella catarrhalis
                ( B ) STRAIN: 25240
                ( C ) CELL TYPE: bacterium ( v ) SEQUENCE DESCRIPTION: SEQ ID NO:10 :

GTTGAATTCA CACCAGTTTG AAAATCCAAG                                                                30

( 2 ) INFORMATION FOR SEQ ID NO:11 :

( i ) SEQUENCE CHARACTERISTICS:
                ( A ) LENGTH: 1650 nucleotides
                ( B ) TYPE: nucleic acid
                ( C ) STRANDEDNESS: double- stranded
                ( D ) TOPOLOGY: linear ( i i ) MOLECULE TYPE: genomic DNA ( i i i ) HYPOTHETICAL: yes ( i v ) IMMEDIATE SOURCE:
                ( A ) LIBRARY: genomic
                ( B ) CLONE: EMBL-3 clone ( v ) ORIGINAL SOURCE:
                ( A ) ORGANISM: Moraxella catarrhalis
                ( B ) STRAIN: 25240
                ( C ) CELL TYPE: bacterium ( v i ) FEATURE:
                ( A ) LOCATION: E gene region, 154- 1531

( v i i ) SEQUENCE DESCRIPTION: SEQ ID NO:11 :

TAAACGCATA AAAATTGTAA GAAAATATAT ATATTTTACT TGTTTTGTGA                   50

-continued

```
TTAAATTTCA TTTAAGATAC AAATGTGTAA GACTTTTGTA CTGTTCTATA        100

AAGAAGTATG GACAGTTTTA CATATTGTAA GGACTGACTT TTTGGAGAAA        150

GTG ATG AGC TTA AAA TTT GGA TAC AAA GCG CTG AGT TTG GCG        192
    Met Ser Leu Lys Phe Gly Tyr Lys Ala Leu Ser Leu Ala
    1           5                   10

GTA TTT TCA ACC CTA ACC GCA ACC GCA GCA CAA GCA GCA GGC        234
Val Phe Ser Thr Leu Thr Ala Thr Ala Ala Gln Ala Ala Gly
    15              20                  25

CTG GAT CGC TCA GGG CAA GAT GTG ACT GCT TTT TTA CAA GAT        276
Leu Asp Arg Ser Gly Gln Asp Val Thr Ala Phe Leu Gln Asp
        30              35                  40

GGC ACT TAT GCC GAA ACC GTT TAT ACT TAT ATT GAT GCC AAT        318
Gly Thr Tyr Ala Glu Thr Val Tyr Thr Tyr Ile Asp Ala Asn
            45              50                  55

GTT ACC GGT AAA GAT ACC GCA GGC AAA GAT ACA GGT GAT ATT        360
Val Thr Gly Lys Asp Thr Ala Gly Lys Asp Thr Gly Asp Ile
                60              65

GCC GAA GCT TAT GAT TTT TTC CGT TAC GGT GTT AAA GCA GAC        402
Ala Glu Ala Tyr Asp Phe Phe Arg Tyr Gly Val Lys Ala Asp
70              75                  80

ATC AAC GAC ACC TTT AGC ATC GGT GTG CTA TAT GAC GAG CCA        444
Ile Asn Asp Thr Phe Ser Ile Gly Val Leu Tyr Asp Glu Pro
    85              90                  95

TTT GGT GCA GCG GTT CAA TAT GAC GGT AAT AGT AAT TTT GTG        486
Phe Gly Ala Ala Val Gln Tyr Asp Gly Asn Ser Asn Phe Val
        100             105                 110

GCA GAT AAA AAT GCA ACA GCA ACA ATT TTT GCC CAA GCT ATC        528
Ala Asp Lys Asn Ala Thr Ala Thr Ile Phe Ala Gln Ala Ile
            115             120                 125

AAT CAG GCT ACA AAA GCA CAA TTA AAC GAT AGC CTT GCT TAT        570
Asn Gln Ala Thr Lys Ala Gln Leu Asn Asp Ser Leu Ala Tyr
                130             135

AAA TCA ATT AAG CCA GTT TTA GAC AGT GTT AAA TCA CCT CAG        612
Lys Ser Ile Lys Pro Val Leu Asp Ser Val Lys Ser Pro Gln
140             145                 150

CGT GCT TTG GCA GTA GCA TCA ATC GTA GAA ACC AAT TCA GCA        654
Arg Ala Leu Ala Val Ala Ser Ile Val Glu Thr Asn Ser Ala
    155             160                 165

CAA GCC AAA CCC ATT GCT GAC CGA TTA AGA GCA GCG GCT GCA        696
Gln Ala Lys Pro Ile Ala Asp Arg Leu Arg Ala Ala Ala Ala
        170             175                 180

CAT GCA GAA GCA ACT GAC GGT CAA AAG ACT AAT GTC GAA ATT        738
His Ala Glu Ala Thr Asp Gly Gln Lys Thr Asn Val Glu Ile
            185             190                 195

CGC ACC AAC AAC CTA ACC ATG TTA GTC GGT GCC AAA TTG GGT        780
Arg Thr Asn Asn Leu Thr Met Leu Val Gly Ala Lys Leu Gly
                200             205

GCT AAT AAA AAT TTC CAA ATC TAT GGC GGT CCT GTG GCT CAA        822
Ala Asn Lys Asn Phe Gln Ile Tyr Gly Gly Pro Val Ala Gln
210             215                 220

AGA GTT AAG GGC GAA GTG CAT TTG CGT GGT CCT GCT TAT CAA        864
Arg Val Lys Gly Glu Val His Leu Arg Gly Pro Ala Tyr Gln
    225             230                 235

GTC ATG ACA GGT TAT GAT GCC AAA ATT GCA ACA GAT ACT CAA        906
Val Met Thr Gly Tyr Asp Ala Lys Ile Ala Thr Asp Thr Gln
        240             245                 250

TTG GGC TGG GCG GCA GGT TTG GCA TTT TAT AAA CCC GAA ATT        948
Leu Gly Trp Ala Ala Gly Leu Ala Phe Tyr Lys Pro Glu Ile
            255             260                 265
```

```
GCC  CTA  AAA  GCC  GCT  TTG  ACC  TAT  CGC  TCT  GAG  ATT  GAG  CAT    990
Ala  Leu  Lys  Ala  Ala  Leu  Thr  Tyr  Arg  Ser  Glu  Ile  Glu  His
          270                           275

GAC  TCT  GAA  ATT  GCC  GAA  ACC  ATT  CCT  GTT  ACG  GGC  TAT  GCG   1032
Asp  Ser  Glu  Ile  Ala  Glu  Thr  Ile  Pro  Val  Thr  Gly  Tyr  Ala
280                      285                      290

GGT  AAA  AAG  GAT  TTT  AAA  GTT  ACT  TTG  CCT  GAC  TCA  TGG  AAC   1074
Gly  Lys  Lys  Asp  Phe  Lys  Val  Thr  Leu  Pro  Asp  Ser  Trp  Asn
     295                      300                      305

TTA  GAT  TTT  CAA  ACT  GGT  GTG  AAT  CCA  ACA  ACG  CTA  TTA  ACT   1116
Leu  Asp  Phe  Gln  Thr  Gly  Val  Asn  Pro  Thr  Thr  Leu  Leu  Thr
          310                      315                      320

GCC  AAA  GTA  CGC  TAT  GTA  CCA  TGG  TCT  GAT  TTT  GAC  ATT  CGC   1158
Ala  Lys  Val  Arg  Tyr  Val  Pro  Trp  Ser  Asp  Phe  Asp  Ile  Arg
               325                      330                      335

CCA  ACA  CAG  TAT  ACA  GAA  ACC  ACA  AAA  CTT  CGT  TAT  CCA  CAG   1200
Pro  Thr  Gln  Tyr  Thr  Glu  Thr  Thr  Lys  Leu  Arg  Tyr  Pro  Gln
                    340                      345

GGT  TTA  CCA  ATC  ATC  AGC  TAT  GAC  AAA  GAC  CAA  TGG  TCG  GCT   1242
Gly  Leu  Pro  Ile  Ile  Ser  Tyr  Asp  Lys  Asp  Gln  Trp  Ser  Ala
350                      355                      360

GAA  GTT  GGT  TTG  GGT  AAG  CGT  GTT  AGC  GAT  CGT  TTG  GCT  GTT   1284
Glu  Val  Gly  Leu  Gly  Lys  Arg  Val  Ser  Asp  Arg  Leu  Ala  Val
     365                      370                      375

TCA  GGT  GCG  GTA  GGT  TGG  GAT  AGT  GGT  GCA  GGT  AAC  CCT  GCA   1326
Ser  Gly  Ala  Val  Gly  Trp  Asp  Ser  Gly  Ala  Gly  Asn  Pro  Ala
          380                      385                      390

AGT  AGC  TTA  GGT  CCT  ATC  AAA  GGC  TAT  TAT  TCA  TTG  GGC  TTA   1368
Ser  Ser  Leu  Gly  Pro  Ile  Lys  Gly  Tyr  Tyr  Ser  Leu  Gly  Leu
               395                      400                      405

GGT  GCG  CGG  TAT  AAT  GTT  ACA  CCT  GAA  TGG  TCG  CTG  TCT  TTG   1410
Gly  Ala  Arg  Tyr  Asn  Val  Thr  Pro  Glu  Trp  Ser  Leu  Ser  Leu
                    410                      415                      420

GGT  GGT  AAA  TAC  TTT  AAA  TTT  GGA  GAT  GCT  CAA  GCA  CAG  CTA   1452
Gly  Gly  Lys  Tyr  Phe  Lys  Phe  Gly  Asp  Ala  Gln  Ala  Gln  Leu
                         425                      430

CCA  ACC  AAA  GAT  AAA  GTA  GGT  AAC  TTT  GAT  AGT  AAT  GAT  GGC   1494
Pro  Thr  Lys  Asp  Lys  Val  Gly  Asn  Phe  Asp  Ser  Asn  Asp  Gly
435                      440                      445

TAT  GCC  TTG  GGC  GTT  AAG  CTT  GCT  TAT  CAC  GCC  AAA  TAATCT     1536
Tyr  Ala  Leu  Gly  Val  Lys  Leu  Ala  Tyr  His  Ala  Lys
     450                      455                      460

CATGCTAAAT  CATACAAAAA  TGTCTAAATA  TAAAAAATAG  CTTGAATTTC             1586

AAGCTATTTT  TTATTAGTTG  GTTAAAAATT  AACGAATCTC  AACCGTCGCA             1636

CATTTCGATG  ACAG                                                       1650
```

( 2 ) INFORMATION FOR SEQ ID NO:12 :

( i ) SEQUENCE CHARACTERISTICS:
        ( A ) LENGTH: 24 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: Moraxella catarrhalis
        ( B ) STRAIN: 25240

( C ) CELL TYPE: bacterium ( v ) SEQUENCE DESCRIPTION: SEQ ID NO:12 :

CGCCAAACTC AGCGCTTTGT ATCC ( 2 ) INFORMATION FOR SEQ ID NO:13 :

( i ) SEQUENCE CHARACTERISTICS:
        ( A ) LENGTH: 24 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: Moraxella catarrhalis
        ( B ) STRAIN: 25240
        ( C ) CELL TYPE: bacterium ( v ) SEQUENCE DESCRIPTION: SEQ ID NO:13 :

GTCAGTCCTT CCAATATGTA AAAC 24

( 2 ) INFORMATION FOR SEQ ID NO:14 :

( i ) SEQUENCE CHARACTERISTICS:
        ( A ) LENGTH: 35 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: Moraxella catarrhalis
        ( B ) STRAIN: 25240
        ( C ) CELL TYPE: bacterium ( v ) SEQUENCE DESCRIPTION: SEQ ID NO:14 :

CGCATAAAAA TTGTAAGAAA ATATATATAT TTTAC 35

( 2 ) INFORMATION FOR SEQ ID NO:15 :

( i ) SEQUENCE CHARACTERISTICS:
        ( A ) LENGTH: 38 nucleotides
        ( B ) TYPE: nucleic acid
        ( C ) STRANDEDNESS: single- stranded
        ( D ) TOPOLOGY: linear ( i i ) MOLECULE TYPE: DNA ( i i i ) IMMEDIATE SOURCE: synthesized ( i v ) ORIGINAL SOURCE:
        ( A ) ORGANISM: Moraxella catarrhalis
        ( B ) STRAIN: 25240
        ( C ) CELL TYPE: bacterium ( v ) SEQUENCE DESCRIPTION: SEQ ID NO:15 :

GCTATTTTTT ATATTTAGAC ATTTTTGTAT GATTTAGC 38

( 2 ) INFORMATION FOR SEQ ID NO:16 :

( i ) SEQUENCE CHARACTERISTICS:
        ( A ) LENGTH: 35 nucleotides
        ( B ) TYPE: nucleic acid
        ( C ) STRANDEDNESS: single- stranded
        ( D ) TOPOLOGY: linear

```
        ( i i ) MOLECULE TYPE: DNA ( i i i ) IMMEDIATE SOURCE: synthesized ( i v ) ORIGINAL SOURCE:
                ( A ) ORGANISM: Moraxella catarrhalis
                ( B ) STRAIN: 25240
                ( C ) CELL TYPE: bacterium ( v ) SEQUENCE DESCRIPTION: SEQ ID NO:16 :

GTGATGAGCT    TAAAATTTGG    ATACAAAGCG    CTGAG                              3 5

( 2 ) INFORMATION FOR SEQ ID NO:17 :

( i ) SEQUENCE CHARACTERISTICS:
                ( A ) LENGTH: 30 nucleotides
                ( B ) TYPE: nucleic acid
                ( C ) STRANDEDNESS: single- stranded
                ( D ) TOPOLOGY: linear ( i i ) MOLECULE TYPE: DNA ( i i i ) IMMEDIATE SOURCE: synthesized ( i v ) ORIGINAL SOURCE:
                ( A ) ORGANISM: Moraxella catarrhalis
                ( B ) STRAIN: 25240
                ( C ) CELL TYPE: bacterium ( v ) SEQUENCE DESCRIPTION: SEQ ID NO:17 :

GCATGAGATT    ATTTGGCGTG    ATAAGCAAGC                                       3 0

( 2 ) INFORMATION FOR SEQ ID NO:18 :

( i ) SEQUENCE CHARACTERISTICS:
                ( A ) LENGTH: 34 nucleotides
                ( B ) TYPE: nucleic acid
                ( C ) STRANDEDNESS: single- stranded
                ( D ) TOPOLOGY: linear ( i i ) MOLECULE TYPE: DNA ( i i i ) IMMEDIATE SOURCE: synthesized ( i v ) ORIGINAL SOURCE:
                ( A ) ORGANISM: Moraxella catarrhalis
                ( B ) STRAIN: 25240
                ( C ) CELL TYPE: bacterium ( v ) SEQUENCE DESCRIPTION: SEQ ID NO:18 :

GCAGGCCTGG    ATCGCTCAGG    GCAAGATGTG    ACTG                               3 4
```

VACCINE FOR MORAXELLA CATARRHALIS

This invention was made with government support under grant A128304 awarded by the National Institutes of Health, and support by the Department of Veteran Affairs. The government has certain rights in the invention.

FIELD OF INVENTION

The present invention relates to compositions comprising a protein, and peptides and oligopeptides thereof, associated with the outer membrane of *Moraxella catarrhalis* (previously referred to as *Branhamella catarrhalis*). More particularly, the invention is directed to compositions of a protein, peptides, and oligopeptides thereof, related to an outer membrane protein, "E", which is a heat-modifiable protein of *M. catarrhalis* having an apparent molecular mass of about 35,000 daltons at 25° C. and about 50,000 daltons when heated to 100°C. Also disclosed is methods for preparing E, E peptides and E oligopeptides using recombinant DNA and/or biochemical techniques. Related thereto, disclosed is the DNA sequence encoding E, and vectors useful in directing the expression of E, E peptides, and E oligopeptides, and host cells transformed with such vectors.

The proteins, peptides, and oligopeptides can be used as immunogens in vaccine formulations for active immunization; and can be used to generate protein-specific and peptide-specific antisera useful for passive immunization, and as reagents for diagnostic assays. The nucleotide sequences disclosed provide for the synthesis of corresponding oligonucleotides which can be used as reagents in diagnostic assays directed to the detection of *M. catarrhalis* genetic material.

BACKGROUND OF THE INVENTION

*Moraxella catarrhalis* (also known as *Branhamella catarrhalis*) is an important human respiratory tract pathogen. *M. catarrhalis* is the third most common cause of otitis media in infants and children, after *Streptococcus pneumoniae* and nontypeable *Haemophilus influenzae*, as documented in studies in which tympanocentesis has been used to establish the etiologic agent (Murphy, 1989, *Pediatr. Infect. Dis. J.* 8:S75–S77). *M. catarrhalis* is a common cause of sinusiris and conjunctivitis in both children and adults (See for example, Bluestone, 1986, *Drugs* 31:S132–S141; Brorson et al., 1976, *Scand. J. Infect. Dis.* 8:151–155; and Romberger et al., 1987, *South. Med. J.* 80:926–928); and is an important cause of lower respiratory tract infections in adults with chronic bronchitis and chronic obstructive pulmonary disease (Murphy et al., 1992, *Am. Rev. Respir. Dis.* 146:1067–1083; Catlin, 1990, *Clin. Microbiol. Rev.* 3:293–320). Additionally, *M. catarrhalis* can cause pneumonia, endocarditis, septicemia, and meningitis in immunocomprised hosts (Cocchi et al., 1968, *Acta Paediatr. Scand.* 57:451-3; Douer et al., 1977, *Ann. Intern. Meal.* 86:116–119; McNeely et al., 1976, *Am. Rev. Respir. Dis.* 114:399–402) .

Since recurrent otitis media is associated with substantial morbidity, there is interest in identifying strategies for preventing these infections. One such approach is the development of vaccines. An effective vaccine for preventing bacterial otitis media would need to include antigens which would generate protection against infection by *S. pneumoniae*, nontypeable *H. influenzae* and *M. catarrhalis*. Indeed, vaccine development for the pneumococcus and nontypeable *H. influenzae* are progressing such that potentially protective antigens have been identified and are currently undergoing testing (See for example, Murphy et al., U.S. Pat. No. 5,173,294; and Vella et al., 1992, *Infect. Immun.* 60:4977–4983). As these vaccines are developed and used more widely, the relative importance of *M. catarrhalis* as a cause of otitis media will increase in the next decade. Besides infants and children benefitting from a vaccine to prevent otitis media caused by *M. catarrhalis*, adults with chronic obstructive pulmonary disease, and immunocompromised children and adults would benefit from a vaccine to prevent infections caused by *M. catarrhalis*.

Bacterial components which have been investigated as potential vaccine antigens include polysaccharides, lipopolysaccharides or modifications thereof, and outer membrane proteins. In general, as exemplified by the type b capsular polysaccharide of *H. influenzas*, polysaccharide antigens have been shown to be a poor immunogen in children under the age of 18 months. Active immunization with lipopolysaccharide (LPS) is unacceptable due to its inherent toxicity. The pathophysiologic effects of LPS may include fever, leucopenia, leucocytosis, the Shwartzman reaction, disseminated intravascular coagulation, and in large doses, shock and death. In general, proteins are immunogenic in infants around three months of age. Thus, outer membrane proteins are being investigated as possible vaccine antigens.

While recent studies have begun to focus on outer membrane proteins of *M. catarrhalis*, little is known about the antigenic and molecular structure of these proteins. Studies of purified outer membranes by sodium dodecyl sulfate polyacrylamide gel electrophoresis (SDS-PAGE) have revealed a rather homogeneous pattern among strains of the bacterium (Bartos and Murphy, 1988, *J. Infect. Dis.* 158:761–765). Eight major outer membrane proteins, designated by the letters A–H, have been identified (Murphy et al., 1989, *Microbial Pathogen.* 6:159–174; Bartos et al., 1988, *J. Infect. Dis.* 158:761–765). Experiments in which 20 strains of *M. catarrhalis* were absorbed with antisera developed against *M. catarrhalis* strain 25240 indicate that outer membrane protein E contains antigenically conserved determinants that are expressed on the bacterial surface (Murphy et al., 1989, *Infect. Immun.* 57:2938–2941).

Hence, with the increasing recognition of *M. catarrhalis* as an important bacterial pathogen, there is a need for a vaccine that is immunogenic in children and adults. Such a vaccine would have to be directed to a bacterial component which has a surface-exposed epitope on intact bacteria, wherein the epitope is conserved amongst strains of *M. catarrhalis*.

SUMMARY OF THE INVENTION

The present invention is directed to a protein, peptides, and oligopeptides related to an outer membrane protein having an apparent molecular mass of about 35,000 daltons to about 50,000 daltons of *M. catarrhalis*, wherein the protein appears to be a heat-modifiable protein resulting in differences in migration in SDS gels, depending on the sample processing temperature. The E protein, and peptides thereof (herein also termed "E peptides" or "E oligopeptides"), of the present invention may be used as immunogens in prophylactic and/or therapeutic vaccine formulations; or as an antigen in diagnostic immunoassays directed to detection of *M. catarrhalis* infection by measuring an increase in serum titer of *M. catarrhalis*-specific antibody. Also, E protein, E peptides and E oligopeptides of the present invention may be used to generate E-specific antibody which may be useful for passive immunization and as reagents for diagnostic assays directed to detecting the presence of *M. catarrhalis* in clinical specimens. E peptides or E oligopeptides can be obtained by chemical synthesis; purification from *M. catarrhalis*; or produced from recombinant vector expression systems using the nucleic acid sequences disclosed herein.

One embodiment of the present invention is directed to the construction of novel DNA sequences and vectors including plasmid DNA, and viral DNA such as human viruses, animal viruses, insect viruses, or bacteriophages which can be used to direct the expression of E protein, E peptides, or E oligopeptides in appropriate host cells from which the expressed protein or peptides may be purified.

Another embodiment of the present invention provides methods for molecular cloning of the gene encoding E, and provides compositions comprising oligonucleotides within the gene sequence encoding E. The nucleic acid sequences of the present invention can be used in molecular diagnostic assays for *M. catarrhalis* genetic material through nucleic acid hybridization, and including the synthesis of E sequence-specific oligonucleotides for use as primers and/or probes in amplifying, and detecting amplified, nucleic acids.

Additionally, E protein, E peptides, and E oligopeptides can be used as immunogens in prophylactic and/or therapeutic vaccine formulations against pathogenic strains of *M. catarrhalis*, whether the immunogen is chemically synthesized, purified from *M. catarrhalis*, or purified from a recombinant expression vector system. Alternatively, the gene encoding E, or one or more gene fragments encoding E peptides or E oligopeptides, may be incorporated into a bacterial or viral vaccine comprising recombinant bacteria or virus which is engineered to produce one or more immunogenic epitopes of E by itself, or in combination with immunogenic epitopes of other pathogenic microorganisms. In addition, the gene encoding E or one or more gene fragments encoding E peptides or E oligopeptides, operatively linked to one or more regulatory elements, can be introduced directly into humans to express protein E, E peptide, or E oligopeptides to elicit a protective immune response.

Figure 1:
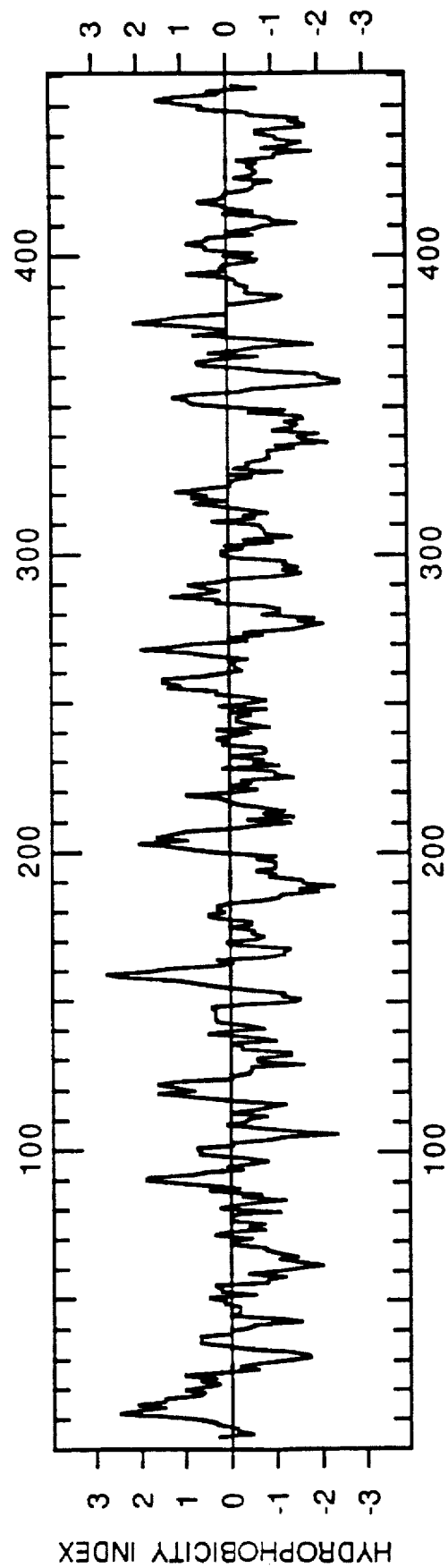
FIG. 1 is a Kay-Doolittle hydrophobicity profile of outer membrane protein E of *M. catarrhalis* as determined using the amino acid sequence deduced from the nucleotide sequence of the gene encoding E. Positive values represent hydrophobic regions and negative values represent hydrophilic regions.

2A is a gel showing the amplified products restricted with Sau96 I.

2B is a gel showing the amplified products restricted with Bsl I.

DETAILED DESCRIPTION OF THE INVENTION

The present invention is directed to compositions of a bacterial outer membrane protein, and peptides thereof, of *M. catarrhalis* wherein the protein has been designated "E". The pattern of migration on SDS-PAGE of the E protein is characteristic of a heat-modifiable protein. That is, the migration pattern depends on the prior sample processing temperature. Thus, if the sample containing E protein is heated at 25° C. prior to SDS-PAGE, the apparent molecular mass is about 35,000 daltons; and if the sample is heated to 100°C., the apparent molecular mass is about 50,000 daltons. As indicated by the nucleotide sequence of the present invention (SEQ ID NO:11), the gene encoding E reveals that the predicted amino acid sequence of the mature E protein has a calculated molecular mass of about 47,030 daltons. The E protein, E peptides, and E oligopeptides of the present invention can be produced using recombinant DNA methods as illustrated herein, or can be synthesized chemically from the amino acid sequence disclosed in the present invention. Additionally, peptides can be produced from enzymatic or chemical cleavage of the mature protein. E protein, E peptides, and E oligopeptides with an immunogenic epitope(s), can be used as immunogens in various vaccine formulations in the prevention of otitis media, sinusiris, conjunctivitis, and lower respiratory tract infections caused by *M. catarrhalis*. Additionally, according to the present invention, the E protein, E peptides, and E oligopeptides produced may be used to generate *M. catarrhalis*-specific antisera useful for passive immunization against infections caused by *M. catarrhalis*.

The present invention further provides the nucleotide sequence of the gene encoding E, as well as the amino acid sequence deduced from the isolated gene. According to one embodiment of the present invention, using recombinant DNA techniques the gene encoding E, or gene fragments encoding one or more E peptides having an immunogenic epitope(s), is incorporated into an expression vector, and the recombinant vector is introduced into an appropriate host cell thereby directing the expression of these sequences in that particular host cell. The expression system, comprising the recombinant vector introduced into the host cell, can be used (a) to produce E protein, E peptides, or E oligopeptides which can be purified for use as an immunogen in vaccine formulations; (b) to produce E protein, E peptides or E oligopeptides to be used as an antigen for diagnostic immunoassays or for generating *M. catarrhalis*-specific antisera of therapeutic and/or diagnostic value; c) or if the recombinant expression vector is a live virus such as vaccinia virus, the vector itself may be used as a live or inactivated vaccine preparation to be introduced into the host's cells for expression of E or immunogenic E peptides or E oligopeptides; d) or if the recombinant expression vector is introduced into live attenuated bacterial cells which are used to express E protein, E peptides or E oligopeptides to vaccinate individuals; e) or introduced directly into an individual to immunize against the encoded and expressed E protein, E peptide, or E oligopeptide.

For purposes of the description, the methods and compounds of the present invention will be illustrated in the following embodiments:

Embodiment A—Molecular cloning and sequencing of the gene encoding E, and vectors expressing E-specific epitopes;

Embodiment B—Conservation of the gene encoding E amongst *M. catarrhalis* strains;

Embodiment C—Methods for using E-specific nucleotide sequences in molecular diagnostic assays for the detection of *M. catarrhalis*;

Embodiment D—Methods for making and using E, E peptides, and E oligopeptides, in diagnostic immunoassays;

Embodiment E—Methods and compounds for vaccine formulations related to E, E peptides, and E oligopeptides.

Embodiment A

Molecular cloning and sequencing of the gene encoding E, and vectors expressing E-specific epitopes.

The strategy used was to isolate genomic DNA from *M. catarrhalis*, cleave the isolated DNA into fragments, construct a genomic library comprising insertion of the fragments into an expression vector, introduce the recombinant vectors into the appropriate host cell, and screen for host cell clones containing the gene encoding E by filter-hybridization with a family of degenerate, labeled oligonucleotides corresponding to the amino terminal sequence of the E protein. The synthesized nucleotides were prescreened by Southern blot to *M. catarrhalis* DNA, and *E. coli* as a control, to determine which degenerate oligonucleotides hybridized strongly to *M. catarrhalis* DNA.

*Moraxella catarrhalis* strain 25240, obtained from the American Type Culture Collection (ATCC) was used as the source of bacterial genomic DNA. *M. catarrhalis* was grown on chocolate agar plates at 37° C. in 5% $CO_2$ or in brain heart infusion broth. *Escherichia coli* (*E. coli*) LE392 was used as the host strain for the bacteriophage lambda (EMBL-3) genomic library. Depending on the circumstances, *E. coli* was grown in tryprone broth supplemented with 0.2% maltose and 10 mM $MgSO_4$; or for screening, on NZCYM agar plates containing 50 82 g/ml of ampicillin.

An EMBL3 genomic library was constructed with genomic DNA of *M. catarrhalis* 25240 using previously described methods (Ausubel et al., 1989, *Current Protocols in Molecular Biology*, published by John Wiley and Sons). Genomic DNA of *M. catarrhalis* strain 25240 was purified using detergent extraction, and proteinase treatment. The purified genomic DNA was then partially digested with restriction enzyme Sau 3A to generate fragments varying in size. The DNA fragments were separated by sucrose gradient centrifugation on a 10% to 40% sucrose gradient. Fractions containing fragments of approximately 9 to 23 kilobases (kb) in size were collected, dephosphorylated using calf intestinal phosphatase, and subsequently ligated to phage arms and then packaged into packge. A portion of the resultant EMBL-3 library was plated on NZCYM plates with *E. coli* LE392 as the host strain.

Plaques were transferred onto nitrocellulose filter discs and screened by hybridization with a family of degenerate radio-labelled oligonucleotides (representative examples disclosed in SEQ ID NO:1–SEQ ID NO:8) corresponding to the amino terminal sequence of outer membrane protein E. A total of about 8100 plaques were screened and six positive clones were identified.

The initial positive plaques were picked, eluted into buffer, and then purified by plating at low density and rescreened with the same oligonucleotides until all the plaques from a rescreening were positive. Liquid lysates of the positive clones were used to isolate the lambda DNA containing the insert. The isolated lambda DNA was then digested with Sal I and the digests were electrophoresed on agarose gels to confirm the presence of inserts. Insert sizes of the positive clones were between 12 kilobases (kb) and 17 kb. The clone containing the 12 kb insert was used to localize the gene encoding E contained within the insert. The DNA from the clone was cut with Sal I and the 12 kb insert was electroeluted from gel slices and restricted with one or more of several different enzymes (Nde I, Nco I, Hind III, Sac I, Eco RI, and Nde I and Nco I). The digests were electrophoresed on agarose gels, and the fragments were analyzed by Southern blot with the oligonucleotide probes.

A 4.4 kb Nde I-Sal I fragment and a 1.9 Nco I- Sal I fragment were selected and manipulated for subcloning into either of the plasmids pET22b$^{+=0}$ or pGEM5zf to facilitate subsequent sequencing. After repeated unsuccessful attempts to transform *E. coli* with the recombinant plasmids, and despite success with control DNA and transformation controls, it was concluded that the fragments containing the gene encoding E, or containing portions thereof, were toxic to the *E. coli*. Thus, an alternative approach was taken to determine the nucleotide sequence. The sequences of the ends of the 1.9 kb fragment were determined by the method of Maxam-Gilbert. The 1.9 kb fragment was digested with Hind III and two fragments were purified, a 1.1 kb fragment and a 0.8 kb fragment. These fragments were labelled and then sequenced using the Maxam-Gilbert method (1977, *Proc. Natl. Acad. Sci. USA* 74:560–564). From this sequence analysis, two additional oligonucleotides were synthesized (SEQ ID NO:9 and SEQ ID NO:10).

Two primers (SEQ ID NO:7 and SEQ ID NO:10) were selected to amplify a fragment of the insert DNA, of the clone having the 12 kb insert, using polymerase chain reaction. The reactions were carried out in a 50 µl volume with 0.25 µg of primers and 2.5 mM dNTP. Pre-denaturing was done at 95° C. for 3 minutes. Denaturing was done at 96° C. for 15 seconds, annealing at 62° C. for 1 minute and polymerization for 74° C. for 1 minute, for 15 cycles in the presence of 3 mM $MgSO_4$. The result of the polymerase chain reaction using these two primers was an amplified product of 0.8 kb. The 0.8 kb amplified product was purified by agarose gel electrophoresis and electroelution, and then subcloned into the Eco RI site of M13mp18. Single-stranded M13 DNA was prepared from the recombinant to determine the nucleotide sequence of the 0.8 kb product by dideoxy-chain termination method. The remaining portion of the gene encoding E was sequenced directly from the 12 kb insert of the lambda clone using additional oligonucleotides synthesized to correspond to the gene region encoding E.

From the complete nucleotide sequence (SEQ ID NO:11), the gene encoding E is defined as an open reading frame of 1377 base pairs (encoding 460 amino acids) starting with the codon at position 154 and ending with TAA at position 1531. A potential ribosome binding site GGAGA was located five bases upstream of the ATG translation initiation codon. Thirty bases downstream of the TAA stop codon was the sequence ATAAAAAATAGCTTGAATTTCAAGC-TATTTTTTAT, a palindrome that could form a stem loop structure which potentially serves as a transcriptional terminator. The overall guanine and cytosine (G+C) content of the gene encoding E is 43.4% which is similar to the reported G+C content of 41% for the *M. catarrhalis* genome (Catlin, 1990, *Clin. Microbiol. Rev.* 3:293–320).

The amino acid sequence, deduced from the open reading frame, defined E as a protein of a calculated molecular mass of 49,334 daltons. The amino acid sequence deduced for E suggested the presence of a signal peptide with a probable cleavage site between amino acids 25 (Ala) and 26 (Ala). The first 24 amino acids from the putative cleavage site, of the amino acid sequence deduced from the open reading frame, corresponds precisely to the N-terminal protein sequence determined from the purified outer membrane protein E. These observations further confirm that the gene encodes E, and that E is synthesized as a precursor possessing a signal peptide composed of 25 amino acid residues. A hydrophobicity profile of the deduced amino acid sequence (FIG. 1) showed a strong hydrophobic portion corresponding to the signal peptide. The predicted antgenic determinants correspond to the hydrophilic regions indicated in FIG. 1. These antigenic determinants include amino acids 369 to 374; 29 to 34; and 294 to 299. The predicted molecular mass of the mature protein is 47,030 daltons, which correlates well with the migration of outer membrane protein E in SDS-PAGE of samples containing *M. catarrhalis*. Analysis of the amino acid composition of E indicated that alanine, glycine, leucine and valine are the most abundant (range 13 %–18%) and no cysteine residues are present.

To determine the transcriptional initiation site of the gene encoding E, primer extension analysis was performed using two different E-specific primers (SEQ ID NO:12 and SEQ ID NO:13) hybridizing to the 5' region of the corresponding mRNA. Total RNA was extracted by the guanidine thiocyanate method from *M. catarrhalis* strain 25240. The E-specific primers were 5' end labeled with [$^{32}$P]ATP. For primer extension, 50 μg of the total RNA was annealed with 100 fmols of the labeled primers and incubated at 55° C. for 45 minutes. This was followed by extension with reverse transcriptase in the presence of deoxyribonucleoside triphosphates for one hour at 42°C. The primer extension product was analyzed on an 8% urea acrylamide sequencing gel. Dideoxy nucleotide sequencing reactions generating a sequencing ladder and primed with the same primers were also electrophoresed in adjacent lanes to assess the exact base for the initiation of the transcript corresponding to E. The results indicate that the transcript starts with a guanine residue at position 75 which is 78 bases upstream of the ATG codon. The potential −10 TAAGAT or the Pribnow box (nucleotide position 63–68) was located six bases upstream of the +1 start site of transcription. The −35 (position 40–45) TTGTT was located seventeen bases upstream of the −10 sequence. Two regions of hyphenated dyad symmetry, 5'TTAATTTCATTTAA-3' and 5' TACAAATGTGTAAGACTTTTGTA-3', were identified downstream of the −35 region which may play a role in regulation of expression of the gene encoding E.

Based on the nucleotide sequence of the gene encoding E, three sets of oligonucleotide primers were synthesized and used to amplify portions of the gene, by polymerase chain reaction, for subcloning and analysis of expression. Two primers (SEQ ID NO:14 and SEQ ID NO:15) were used to amplify 1.573 kb of the gene, the amplified fragment containing the complete gene and the promoter region. Another set of primers (SEQ ID NO:16 and SEQ ID NO:17) were used to amplify 1.391 kb of the gene which contained sequence encoding the leader peptide along with the rest of the gene. A third set of primers (SEQ ID NO:17 and SEQ ID NO:18) were used to amplify 1.313 kb of the gene encoding from the first amino acid of the mature protein to the end of the carboxy terminus. The three amplified products, 1.573 kb, 1.391 kb, and 1.313 kb, were separately subcloned into a vector, phagemid pCR-Script SK$^+$, and transformed into *E. coli* using standard protocols. Attempts at transformation with the recombinant plasmid containing the 1.573 kb fragment were unsuccessful suggesting, again, that expression of *M. catarrhalis* protein E in *E. coli* is toxic to the transformed bacteria. Transformants were identified that contained recombinant plasmids with the 1.391 kb insert (the entire open reading frame without the promoter) and the 1.313 kb insert (sequence encoding the mature protein). Confirmation of the inserts, by sequencing the ends of the inserts, indicated that all identified clones contained the gene sequences in the wrong orientation for expression of the protein by the plasmid promoter; further evidence that the expression of protein E is toxic to *E. coli*.

Thus, this embodiment illustrates that nucleotide sequences encoding E or portions thereof, can be inserted into various vectors including phage vectors and plasmids. Successful expression of the protein and peptides of protein E requires that either the insert comprising the gene or gene fragment which encodes epitopes of protein E, or the vector itself, contain the necessary elements for transcription and translation which is compatible with, and recognized by the particular host system used for expression. DNA encoding E protein, E peptides, or E oligopeptides can be synthesized or isolated and sequenced using the methods and primer sequences as illustrated according to Embodiments A, B, and E herein. A variety of host systems may be utilized to express E protein, E peptides or E oligopeptides, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the DNA sequence encoding E amino acid sequences, i.e. recombinant outer membrane protein E, E peptide or E oligpeptide, to increase the expression of E amino acid sequence, provided that the increased expression of the E amino acid sequences is compatible with (for example, non-toxic to) the particular host cell system used. Thus and importantly, the DNA sequence can consist of the gene encoding E protein, or any segment of the gene which encodes a functional epitope of the E protein. Further, the DNA can be fused to DNA encoding other antigens, such as other bacterial outer membrane proteins, or other bacterial, fungal, parasitic, or viral antigens to create a genetically fused (sharing a common peptide backbone) multivalent antigen for use as an improved vaccine composition.

The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted DNA sequence encoding E amino acid sequences.

Additionally, if E protein, E peptides, or E oligopeptides may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside). A variety of operons such as the trp operon, are under different control mechanisms. The trp operon is induced when tryptophan is absent in the growth media. The $P_L$ promoter can be induced by an increase in temperature of host cells containing a temperature sensitive lambda repressor. In this way, greater than 95% of the promoter-directed transcription may be inhibited in uninduced cells. Thus expression of recombinant E, E peptides, or E oligopeptides may be controlled by culturing transformed or transfected cells under conditions such that the promoter controlling the expression from the inserted DNA encoding E amino acids is not induced, and when the cells reach a suitable density in the growth medium, the promoter can be induced for expression from the inserted DNA.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted DNA sequences encoding E amino acids to increase transcriptional efficiency. As illustrated previously in this embodiment, other specific regulatory sequences have been identified which may effect the expression from the gene encoding E. These or other regulatory sites, such as transcription or translation initiation signals, can be used to regulate the expression of the gene encoding E, or gene fragments thereof. Such regulatory elements may be inserted into DNA sequences encoding E amino acids or nearby vector DNA sequences using recombinant DNA methods described herein for insertion of DNA sequences.

Accordingly, *M. catarrhalis* nucleotide sequences containing regions encoding for E, E peptides, or E oligopeptides can be ligated into an expression vector at a specific site in relation to the vector's promoter, control, and regulatory elements so that when the recombinant vector is introduced into the host cell, the *M. catarrhalis* E-specific DNA sequences can be expressed in the host cell. For example, the E-specific DNA sequences containing its own regulatory elements can be ligated into an expression vector in a relation or orientation to the vector promoter, and control elements which will allow for expression of E amino acid sequences. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid, immuno-screening for production of E-specific epitopes using antisera generated to E-specific epitopes, and probing the DNA of the host's cells for E-specific nucleotide sequences using one or more oligonucleotides and methods described according to Embodiment C herein.

Genetic engineering techniques may also be used to characterize, modify and/or adapt the encoded E peptides or E proteins. For example, site-directed mutagenesis to modify an outer membrane protein fragment in regions outside the protective domains, may be desirable to increase the solubility of the subfragment to allow for easier purification. Further, genetic engineering techniques can be used to generate DNA sequences encoding a portion of the amino acid sequence of E. For example, from the sequence disclosed as SEQ ID NO:11, it can be determined which restriction enzyme or combination of restriction enzymes may be used to generate sequences encoding E peptides or E oligopeptides. Restriction enzyme selection may be done so as not to destroy the immunopotency of the resultant peptide or oligpeptide. Antigenic sites of a protein may vary in size but can consist of from about 7 to about 14 amino acids. Thus, a protein the size of E may contain many discrete antigenic sites; therefore, many partial gene sequences could encode antigenic epitopes of E. Consequently, using FIG. 1 and SEQ ID NO:11 as guides, restriction enzyme combinations may be used to generate DNA sequences, which when inserted into the appropriate vector, are capable of directing the production of E-specific amino acid sequences (peptides or oligopeptides) comprising different antigenic epitopes.

Embodiment B

Conservation of the gene encoding E amongst *M. catarrhalis* strains.

Figure 2A:
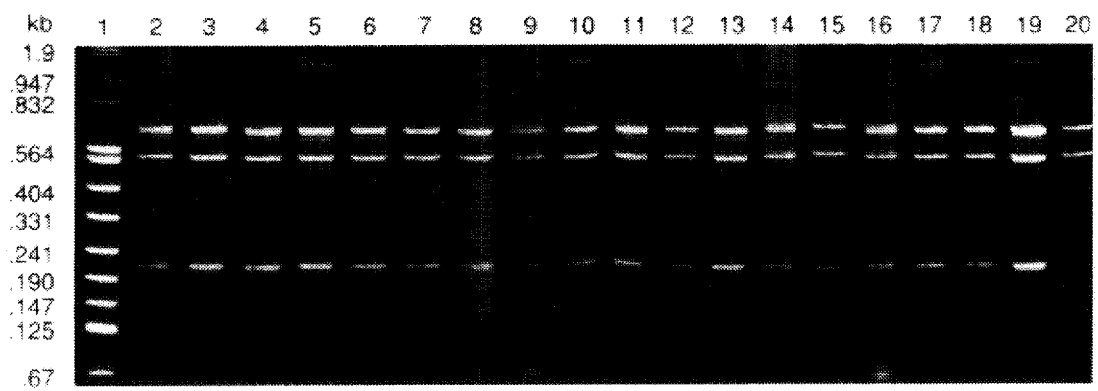
FIG. 2 represents polyacrylamide gels stained with ethidium bromide and containing amplified product from the genomes of different strains of *M. catarrhalis* after digestion with various restriction enzymes. Lane 1 represents DNA size standards, and lanes 2–20 are amplified products from strains listed in Table 1, respectively.
Figure 2B:
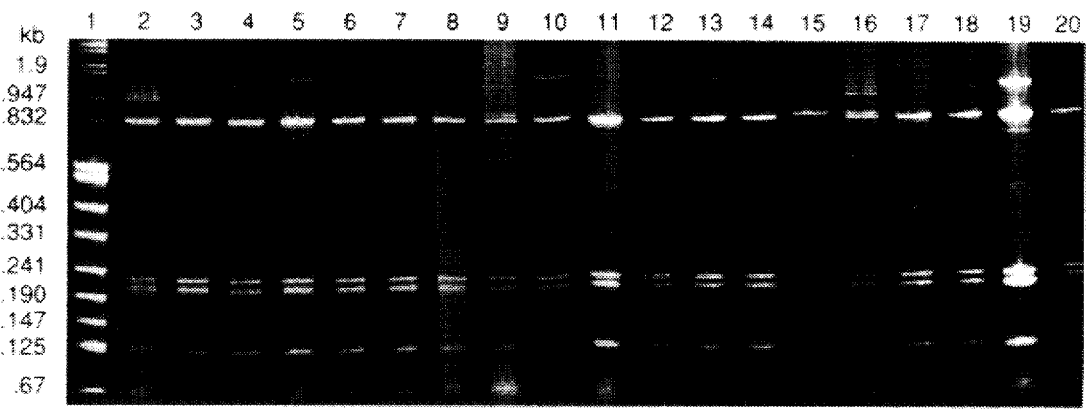

Previous studies, using antibody adsorption experiments, demonstrated that one or more of the surface-exposed determinants of *M. catarrhalis* were antigenically conserved among most strains (Murphy et al., 1989, supra). However, these studies did not address the conservation of the gene encoding E amongst strains. For the nucleotide sequences of the present invention to be useful in diagnostic assays, the gene encoding E must be highly conserved amongst strains of *M. catarrhalis*. In addition, a highly conserved gene indicates that the protein sequence is also highly conserved. For a bacterial protein or peptide to be useful as an antigen in vaccine formulations against infection caused by *M. catarrhalis*, the protein or peptide must contain epitopes that are both immunogenic, and conserved amongst strains of *M. catarrhalis*. To determine the degree of conservation of the gene encoding E among strains of *M. catarrahlis*, genomic DNA was purified and analyzed from 19 isolates recovered from diverse clinical and geographic sources. First, the E-specific gene sequences from the purified DNA of the isolates were amplified using the polymerase chain reaction and primers (SEQ ID NO:16 and SEQ ID NO:17). Analysis of the amplified products, by agarose gel electrophoresis, showed that the gene encoding E was the same size (approximately 1.4 kb) in all the strains tested. Additionally, restriction fragment length polymorphisms were analyzed by restricting the amplified products into fragments using either Hind III, Sau96 I, Bsl I, or Bsg I, and visualizing the fragments by electrophoresis on a 6% acrylamide gel stained with ethidium bromide. The banding pattern of the amplified products showed no variation among the strains tested with regard to the presence of the restriction sites and minimal differences in the observed size of the fragments (as illustrated in FIG. 2A for Sau96 I, and FIG. 2b for Bsl I). Of the four different enzymes used in the restriction of the amplified products, three of the enzymes cut at three different sites within the amplified products, and one cuts at two different sites. Thus, the similar results in all strains indicate that the sequences recognized at the eleven sites are identical among strains tested. The strains listed in Table 1 are the strains tested for restriction fragment length polymorphisms, in the same order as they appear on the gels (shown in FIG. 2A and FIG. 2B, beginning with lane 2). Differences in restriction patterns among different strains may exist, but differences were not seen with these particular restriction enzymes tested.

TABLE 1

| Isolates of *Moraxella catarrhalis* | |
|---|---|
| Strain Designation | Clinical Sources |
| Tal 2 | sinus |
| 58 | sputum |
| 3584 | middle ear fluid |
| 9483 | middle ear fluid |
| 45 | sputum |
| 690 | sputum |

TABLE 1-continued

Isolates of *Moraxella catarrhalis*

| Strain Designation | Clinical Sources |
| --- | --- |
| 621 | sputum |
| 56 | sputum |
| 1 | transtracheal aspirate |
| 42 | sputum |
| 931 | sputum |
| 701 | sputum |
| 14 | sputum |
| 135 | middle ear fluid |
| 7221 | middle ear fluid |
| 585 | blood |
| 555 | middle ear fluid |
| 25240 | ATCC isolate |
| 5191 | middle ear fluid |

These findings indicate that the gene encoding E is highly conserved amongst strains of *M. catarrhalis*, and therefore the nucleotide sequences described herein have applications for diagnostic and vaccine use.

Embodiment C

Methods for using E-specific nucleotide sequences in molecular diagnostic assays for the detection of *M. catarrhalis*.

Because of the conservation of the gene encoding E, as disclosed in Embodiment B, the nucleic acid sequences of the present invention can be used in molecular diagnostic assays for detecting *M. catarrhalis* genetic material. In particular, and as illustrated by SEQ ID NO:1–SEQ ID NO:10 and SEQ ID NO:12–SEQ ID NO:18, E sequence-specific oligonucleotides can be synthesized for use as primers and/or probes in amplifying, and detecting amplified, nucleic acids from *M. catarrhalis*. Recent advances in molecular biology have provided several means for enzymatically amplifying nucleic acid sequences. Currently the most commonly used method, PCR™ (polymerase chain reaction, Cetus Corporation) involves the use of a thermostable DNA Polymerase, known sequences as primers, and heating cycles which separate the replicating deoxyribonucleic acid (DNA) strands and exponentially amplify a gene of interest. Other amplification methods currently under development include LCR™ (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA™ (nucleic acid sequence-based amplification, Cangene Corporation) which can be performed on RNA or DNA as the nucleic acid sequence to be amplified.

Nucleic acid probes that are capable of hybridization with specific gene sequences have been used successfuly to detect specific pathogens in biological specimens at levels of sensitivity approaching $10^{3-10^4}$ organisms per specimen (1990, *Gene Probes for Bacteria*, eds. Macario and deMacario, Academic Press). Coupled with a method that allows for amplification of specific target DNA sequences, species-specific nucleic acid probes can greatly increase the level of sensitivity in detecting organisms in a clinical specimen. Use of these probes may allow direct detection without relying on prior culture and/or conventional biochemical identification techniques. This embodiment of the present invention is directed to primers which amplify species-specific sequences of the gene encoding E of *M. catarrhalis*, and to probes which specifically hybridize with these amplified DNA fragments. By using the nucleic acid sequences of the present invention and according to the methods of the present invention, as few as one *M. catarrhalis* organism may be detected in the presence of 10 µg/ml extraneous DNA.

This embodiment is directed to species-specific oligonucleotides which can be used to amplify sequences of *M. catarrhalis* DNA, if present, from DNA extracted from clinical specimens including middle ear fluid, sputum, blood, and fluids from the nasopharynx, eye, and adenoid; and to subsequently determine if amplification has occurred. In one embodiment of the present invention, a pair of *M. catarrhalis*-specific DNA oligonucleotide primers are used to hybridize to *M. catarrhalis* genomic DNA that may be present in DNA extracted from a clinical specimen, and to amplify the specific segment of genomic DNA between the two flanking primers using enzymatic synthesis and temperature cycling. Each pair of primers are designed to hybridize only to the *M. catarrhalis* nucleotide sequences comprising the gene encoding E (i.e. within the region of the genome containing SEQ ID NO:11) to which they have been synthesized to complement; one to each strand of the double-stranded DNA. Thus, the reaction is specific even in the presence of microgram quantities of heterologous DNA. For the purposes of this description, the primer derived from the sequence of the positive (gene) strand of DNA will be referred to as the "positive primer", and the primer derived from the sequence of the negative (complementary) strand will be referred to as the "negative primer".

Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the *M. catarrhalis* DNA sequences, if present, results. Further identification of the amplified DNA fragment, as being derived from *M. catarrhalis* DNA, may be accomplished by liquid hybridization. This test utilizes one or more labeled oligonucleotides as probes to specifically hybridize to the amplified segment of *M. catarrhalis* DNA. Detection of the presence of sequence-specific amplified DNA may be accomplished using any one of several methods known in the art such as a gel retardation assay with autoradiography. Thus, the nucleotide sequences of the present invention provide basis for the synthesis of oligonucleotides which have commercial applications in diagnostic kits for the detection of *M. catarrhalis*. In a related embodiment, the oligonucleotides used as primers may be labeled directly, or synthesized to incorporate label. Depending on the label used, the amplification products can then be detected, after binding onto an affinity matrix, using isotopic or colorimetric detection.

DNA may be extracted from clinical specimens which may contain *M. catarrhalis* using methods known in the art. For example, cells contained in the specimen may be washed in TE buffer and pelleted by centrifugation. The cells then may be resuspended in 100 µl of amplification reaction buffer containing detergents and proteinase K. Using the polymerase chain reaction, the resultant sample may be composed of the cells in 10 mM Tris pH 8.3, 50 mM KCl, 1.5 mM MgCl$_2$, 0.01% gelatin, 0.45% NP40™, 0.045% Tween 20™, and 60 µg/ml proteinase K. The sample is incubated at 55° C. water bath for 1 hour. Following the incubation, the sample is incubated at 95° C. for 10 minutes to heat-inactivate the proteinase K. The sample may then be amplified in accordance with the protocol for the polymerase chain reaction as set forth below.

The *M. catarrhalis* DNA may be amplified using any one of several protocols for amplifying nucleic acids by the polymerase chain reaction. In one mode of this embodiment, the gene encoding E was amplified from 19 clinical isolates of *B. catarrhalis* using the following conditions. DNA to be amplified (≈1 µg of genomic DNA) was distributed in 0.5 ml microfuge tubes and the volume was adjusted to 50 µl by adding a reaction mixture comprising 0.2 mM dNTPs (dATP, dCTP, dGTP, dTTP), 0.25 µg of each positive and negative oligonucleotide primer, 1 unit of thermostable DNA polymerase, polymerase 10×buffer (5 µl), 3 mM MgSO$_4$ (final concentration), and sterile distilled water to achieve the total volume. The DNA polymerase is added to the reaction mixture just before use and is gently mixed, not vortexed. A layer of mineral oil, approximately 2 drops, is added to each tube and then the tubes are placed in the thermal cycler. Thirty to thirty-five cycles are generally sufficient for bacterial DNA amplification.

One cycle consists of 15 seconds at 96° C., 1 minute at 62° C., and 1 minute at 74° C. The first cycle includes a 3 minute incubation at 95° C. to assure complete denaturation.

Oligonucleotides useful as primers or probes which specifically hybridize to the gene encoding E of *M. catarrhalis* and used in DNA amplification and/or detection can be biochemically synthesized, using methods known in the art, from the nucleotide sequences disclosed in the present invention. The specificity of the oligonucleotides for *M. catarrhalis* can be checked by a genebank database (Genbank) search for each individual sequence. In general, the oligonucleotides should be selected for low G-C content. Pairs of primers that have been used for this embodiment to amplify the whole gene encoding E include SEQ ID NO:14 and SEQ ID NO:15. Pairs of primers used to amplify portions of the gene include SEQ ID NO:16 and SEQ ID NO:17; and SEQ ID NO:17 and SEQ ID NO:18.

For detection purposes, the oligonucleotides of the present invention may be end-labeled with a radioisotope. Probe sequences, internal to the two primers used for amplification of the gene sequence, may be end-labeled using T4 polynucleotide kinase and gamma $^{32}$P ATP. Twenty pMols of probe DNA in kinase buffer (50 mM Tris, pH 7.6, 10 mM MgCl$_2$, 5 mM dithiothreitol, 0.1 mM spermidine-HCl, 0.1 mM EDTA, pH 8.0) is mixed with 120 µCi of gamma $^{32}$P ATP and incubated at 37° C. for 1 hour. Labeled probe is separated from unincorporated label on an 8% acrylamide gel run for 1 hour at 200 volts in Tris Borate EDTA (TBE) buffer at room temperature. Labeled probe is first located by exposing the acrylamide gel to x-ray film for three minutes. The resulting autoradiogram is then positioned under the gel, and the band containing the labeled probe was excised from the gel. The gel slice is pulverized in one milliliter of sterile distilled water, and the probe is eluted by shaker incubation overnight at 37° C. The eluted probe is separated from the gel fragments by centrifugation using a chromatography prep column. Radioactivity of the probe is determined, by counting one microliter of the labeled probe on a glass fiber filter, by liquid scintillation. Such probe sequences may be chosen from any of the sequences identified as SEQ ID NO: 1 to SEQ ID NO:10, and SEQ ID NO:12 to SEQ ID NO:18 provided the probe sequence is internal to the two primers used for amplification of the desired nucleotide sequence disclosed in the present invention.

Alternative methods known in the art may be used to improve the detection of amplified target sequences in accordance with the compositions and methods of the present invention. The sensitivity of detection of the amplified DNA sequences can be improved by subjecting the sequences to liquid hybridization. Alternative methods of detection known in the art, in addition to gel electrophoresis and gel electrophoresis with Southern hybridization and autoradiography, that may be used with the compositions and methods of the present invention include: restriction enzyme digestion with gel electrophoresis; slot-blot hybridization with a labeled oligonucleotide probe; amplification with a radiolabeled primer with gel electrophoresis, Southern hybridization and autoradiography; amplification with a radiolabeled primer with dot blot and autoradiography; amplification with oligonucleotides containing affinity tags (ex. biotin, or one primer incorporating biotin and the other primer with a sequence specific for a DNA binding protein) followed by detection in an affinity-based assay (ex. ELISA); and amplification with nucleotides containing fluorophores followed by fluorescence detection.

One embodiment of non-isotopic detection involves incorporating biotin into the oligonucleotide primers of the present invention. The 5'-aminogroup of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA from a clinical specimen. The detection for the presence or absence of amplified target sequences may be accomplished by capturing the amplified target sequences using an affinity matrix having avidin bound thereto, followed by incubation with an avidin conjugate containing an enzyme which can be used to visualize the complex with subsequent substrate development.

Alternately, the amplified target sequences may be immobilized by hybridization to the corresponding probes of the target sequence wherein the probes have been affixed onto a matrix. Detection may be accomplished using an avidin conjugate containing an enzyme which can be used to visualize the complex with subsequent substrate development.

Embodiment D

Methods for making and using E, E peptides, or E oligopeptides in diagnostic immunoassays.

E protein, E peptides, and E oligopeptides can be purified for use as an immunogen in vaccine formulations; and as an antigen for diagnostic assays or for generating *M. catarrhalis*-specific antisera of therapeutic and/or diagnostic value. E protein from *M. catarrhalis* or peptides thereof, or recombinant E protein, recombinant E peptides, or recombinant E oligopeptides produced from an expression vector system, can be purified with methods known in the art including detergent extraction, chromatography (e.g., ion exchange, affinity, immunoaffinity, or sizing columns), differential centrifugation, differential solubility, or other standard techniques for the purification of proteins. For example, a partially purified preparation, containing primarily bacterial outer membrane proteins, can be prepared as follows. Bacteria expressing E from 30 chocolate agar plates were scraped into 25 ml of PBS, pH 7.2, and harvested by centrifugation at 12,000×g for 20 minutes at 4° C. The bacterial pellet was resuspended in 10 ml of 1M sodium acetate-0.001M β-mercaptoethanol (pH 4.0). A 90-ml volume of a solution containing 5% Zwittergent Z 3–14 (Calbiochem-Behring) and 0.5% M CaCl$_2$ was added, and the suspension was mixed for 1 hour at room temperature. Nucleic acids were precipitated by the addition of 25 ml cold ethanol and subsequent centrifugation at 17,000×g for 10 minutes at 4° C. The remaining proteins were precipitated by the addition of 375 ml cold ethanol and collected by centrifugation at 17,000×g for 20 minutes at 4° C. The pellets were allowed to dry and were then suspended in 10 ml of detergent buffer containing 0.05% Zwittergent, 0.05M Tris, 0.01M EDTA, pH 8.0, and mixed for 1 hour at room temperature. The bacterial outer membrane proteins are present in the soluble fraction of the detergent buffer after centrifugation at 12,000×g for 10 minutes at 4° C.

Immunopurification of the E protein from an outer membrane protein preparation may be accomplished using methods known in the art for immunoaffinity chromatography. E-specific monoclonal antibodies may be linked to a chromatographic matrix to form an affinity matrix. The outer membrane protein preparation is then incubated with the affinity matrix allowing the antibodies to bind to E. The affinity matrix is then washed to remove unbound components and E is then eluted from the affinity matrix resulting in a purified preparation of E protein. The purified E may be used as an antigen for diagnostic assays, or may be chemically or enzymatically cleaved into peptides using methods known to those in the art. Alternatively, E peptides, or oligopeptides, may be chemically synthesized using the deduced amino acid sequence from the gene encoding E as a reference. Recombinant E protein may be purified using similar methods.

E oligopeptides are defined herein as a series of peptides corresponding to a portion of the amino acid sequence of E protein as disclosed in SEQ ID NO:11 that are synthesized as one or chemically-linked. Such peptides or oligopeptides can be synthesized using one of the several methods of peptide synthesis known in the art including standard solid peptide synthesis using tert-butyloxycarbonyl amino acids (Mitchell et al., 1978, *J. Org. Chem.* 43:2845–2852), using 9-fluorenylmethyloxycarbonyl amino acids on a polyamide support (Dryland et al., 1986, *J. Chem. So. Perkin Trans. I,* 125–137); by pepscan synthesis (Geysen et al., 1987, *J. Immunol. Methods* 03:259; 1984, *Proc. Natl. Acad. Sci.* USA 81:3998); or by standard liquid phase peptide synthesis. Modification of the peptides or oligopeptides, such as by deletion and substitution of amino acids (and including extensions and additions to amino acids) and in other ways, may be made so as to not substantially detract from the immunological properties of the peptide or oligpeptide. In particular, the amino acid sequence of the E protein may be altered by replacing one or more amino acids with functionally equivalent amino acids resulting in an alteration which is silent in terms of an observed difference in the physicochemical behavior of the protein, peptide, or oligpeptide.

Purified E protein, E peptides, and E oligopeptides may be used as antigens in immunoassays for the detection of *Moraxella catarrhalis*-specific antisera present in the body fluid of an individual suspected of having an infection caused by *M. catarrhalis.* The body fluids include, but are not limited to, middle ear fluid, sputum, blood, and fluids from the nasopharynx, eye, and adenoid. The detection of E, E peptides, or E oligopeptides as an antigen in immunoassays, includes any immunoassay known in the art including, but not limited to, radioimmunoassay, enzyme-linked immunosorbent assay (ELISA), "sandwich" assay, precipitin reaction, agglutination assay, fluorescent immunoassay, and chemiluminescence-based immunoassay.

Embodiment E

Methods and compounds for vaccine formulations related to E, E peptides, and E oligopeptides.

This embodiment of the present invention is to provide E protein and/or peptides thereof, to be used in as immunogens in a prophylactic and/or therapeutic vaccine for active immunization to protect against or treat infections caused by *M. catarrhalis.* For vaccine development, the E-specific amino acid sequences comprising the immunogen may be purified from *M. catarrhalis* or may be purified from a host containing a recombinant vector which expresses E, E peptides, or E oligopeptides. Such hosts include, but are not limited to, bacterial transformants, yeast transformants, filamentous fungal transformants, and cultured cells that have been either infected or transfected with a vector which encodes E amino acid sequences. Peptides or oligopeptides corresponding to portions of the E protein may be produced from chemical or enzymatic cleavage of E protein, or chemically synthesized using methods known in the art and with the amino acid sequence deduced from the nucleotide sequence of the gene encoding E as a reference. Alternatively, E peptides or E oligopeptides may be produced from a recombinant vector. In either case, the E protein, E peptide or E oligpeptide immunogen is included as the relevant immunogenic material in the vaccine formulation, and in therapeutically effective amounts, to induce an immune response. Many methods are known for the introduction of a vaccine formulation into the human or animal to be vaccinated. These include, but are not limited to, intradermal, intramuscular, intraperitoneal, intravenous, subcutaneous, ocular, intranasal, and oral administration. The vaccine may further comprise a physiological carrier such as a solution, a polymer or liposomes; and an adjuvant, or a combination thereof.

Various adjuvants are used in conjunction with vaccine formulations. The adjuvants aid in attaining a more durable and higher level of immunity using smaller amounts of vaccine antigen or fewer doses than if the vaccine antigen were administered alone. The mechanism of adjuvant action is complex and not completely understood. However, it may involve immunomodulation through the stimulation of cytokine production, phagocytosis and other activities of the reticuloendothelial system, as well as delayed release and degradation/processing of the antigen to enhance immune recognition. Examples of adjuvants include incomplete Freund's adjuvant, Adjuvant 65 (containing peanut oil, mannide monooleate and aluminum monostearate), oil emulsions, Ribi adjuvant, the pluronic polyols, polyamines, Avridine, Quil A, saponin, MPL, QS-21, and mineral gels such as aluminum hydroxide, aluminium phosphate, etc.

Another embodiment of this mode of the invention involves the production of E-specific amino acid sequences as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such a E-specific hapten liked to a carrier molecule may be the immunogen in a vaccine formulation.

Another mode of this embodiment provides for either a live recombinant viral vaccine, recombinant bacterial vaccine, recombinant attenuated bacterial vaccine, or an inactivated recombinant viral vaccine which is used to protect against infections caused by *M. catarrhalis*. Vaccinia virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens such as E, or E peptides, thereby providing long-lasting immunity.

Other live vaccine vectors include: adenovirus, coytomegalovirus, and preferably the poxviruses such as vaccinia (Paoletti and Panicali, U.S. Pat. No. 4,603,112) and attenuated Salmonella strains (Stocker et al., U.S. Pat. Nos. 5,210,035; 4,837,151; and 4,735,801; and Curtiss et al., 1988, *Vaccine* 6:155–160). Live vaccines are particularly advantageous because they continually stimulate the immune system which can confer substantially long-lasting immunity. When the immune response is protective against subsequent *M. catarrahlis* infection, the live vaccine itself may be used in a preventative vaccine against *M. catarrhalis*.

To illustrate this mode of the embodiment, using molecular biological techniques such as those illustrated in Embodiment A, the gene encoding E, or a gene fragment encoding one or more E peptides may be inserted into the vaccinia virus genomic DNA at a site which allows for expression of E epitopes but does not negatively affect the growth or replication of the vaccinia virus vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen and without substantially affecting the immunogenicity of the expressed immunogen. A mixture of inactivated viruses which express different epitiopes may be used in the formulation of a multivalent inactivated vaccine. In either case, the inactivated recombinant vaccine or mixture of inactivated viruses may be formulated with a suitable adjuvant in order to enhance the immunological response to the vaccine antigens.

In another variation of this embodiment, genetic material is used directly as the vaccine formulation. Nucleic acid (DNA or RNA) containing sequences encoding E, E peptide or E oligpeptide, operatively linked to one or more regulatory elements can be introduced directly to vaccinate the individual ("direct gene transfer") against pathogenic strains of *M. catarrahlis*. Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid:cationic liposome complex (Zhu et al., 1993, *Science* 261:209–211). Other effective methods for delivering vector DNA into a target cell are known in the art. In one example, purified recombinant plasmid DNA containing viral genes has been used to inoculate (whether parentally, mucosally, or via gene-gun immunization) vaccinees to induce a protective immune response (Fynan et al., 1993, *Proco Natl. Acad. Sci. USA* 90:11478–11482). In another example, cells removed from an individual can be transfected or electroporated by standard procedures known in the art, resulting in the introduction of the recombinant vector DNA into the target cell. Cells containing the recombinant vector DNA may then be selected for using methods known in the art such as via a selection marker expressed in the vector, and the selected cells may then be re-introduced into the individual to express E protein, E peptide, or E oligpeptide.

One preferred method of vaccination with genetic material comprises the step of administering to the individual the nucleic acid molecule that comprises a nucleic acid sequence that encodes for one or more of the E protein, E peptides, or E oligopeptides, wherein the nucleic acid molecule is operatively linked to one or more regulatory sequences necessary for expression. The nucleic acid molecule can be administered directly, or first introduced into a viral vector and administered via the vector. The nucleic acid molecule can be administered in a pharmaceutically acceptable carrier or diluent and may contain compounds that can enhance the effectiveness of the vaccine. These additional compounds include, but are not limited to, adjuvants that modulate and enhance the immune response, or other compounds which increase the uptake of nucleic acid by the cells. The immunization with the nucleic acid molecule can be through any parental route (intravenous, intraperitoneal, intradermal, subcutaneous, or intramuscular), or via contact with mucosal surfaces of the nasopharynx, trachea, or gastrointestinal tract.

As an alternative to active immunization, such as where an immunocompromised individual is suffering from a potentially life-threatening infection caused by *M. catarrhalis*, immunization may be passive, i.e. immunization comprising administration of purified human immunoglobulin containing antibody against E epitopes.

It should be understood that while the invention has been described in detail herein, the examples were for illustrative purposes only. Other modifications of the embodiments of the present invention that are obvious to those skilled in the art of molecular biology, medical diagnostics, and related disciplines are intended to be within the scope of the appended claims.

What is claimed is:

1. A recombinant vector comprising a DNA sequence encoding one or more antigenic determinants or epitopes of E, wherein E is an outer membrane protein of *Moraxella catarrhalis* of an apparent molecular mass of from about 35,000 to about 50,000 daltons by SDS-PAGE and having an amino acid sequence comprising SEQ ID NO:11 from amino acid residue 26 to 460.

2. The recombinant vector of claim 1, wherein the vector is selected from the group consisting of a plasmid vector, phagemid vector, cosmid vector, and a viral vector.

3. An isolated nucleic acid molecule selected from the group consisting of a gene and a fragment thereof, wherein said gene comprises a 1377 base pair open reading frame of SEQ ID NO:11 and encodes outer membrane protein E of *Moraxella catarrhalis*, said protein having an apparent molecular mass of from about 35,000 to about 50,000 daltons by SDS-PAGE, and wherein the fragment encodes an antigenic epitope of outer membrane protein E, said epitope consists of from about 7 about 14 amino acids.

4. An infectious, recombinant microorganism containing a nucleic acid molecule encoding an E amino acid sequence selected from the group consisting of E protein, E peptides and E oligopeptides of *M. catarrhalis*, wherein the recombinant microorganism expresses the E amino acid sequence under suitable growth conditions.

5. A microorganism of claim 4, which is a bacterium of the genus Salmonella.

6. An infectious, recombinant virus containing a nucleic acid molecule encoding an E amino acid sequence selected from the group consisting of E protein, E peptides and E oligopeptides of *M. catarrhalis*, wherein the recombinant virus expresses the E amino acid sequence under suitable conditions.

7. A virus of claim 6, which is vaccinia virus, adenovirus, or cytomegalovirus.

8. A method of producing one or more antigenic determinants or epitopes of outer membrane protein E of *Moraxella catarrhalis*, said method comprises introducing the recombinant vector according to claim 1 into a host cell, and culturing the host cell containing the recombinant vector under conditions which permit expression of said one or more antigenic determinants.

* * * * *

UNITED STATES PATENT AND TRADEMARK OFFICE
CERTIFICATE OF CORRECTION

PATENT NO. : 5,607,846
DATED : March 4, 1997
INVENTOR(S) : Murphy et al.

Page 1 of 2

It is certified that error appears in the above-indentified patent and that said Letters Patent is hereby corrected as shown below:

col. 6, line 42, "460" should be --459-- col. 27 and 28, lines 31-42, the amino acids should be numbered as

```
GGT GCG CGG TAT AAT GTT ACA CCT GAA TGG TCG CTG TCT TTG  1410
Gly Ala Arg Tyr Asn Val Thr Pro Glu Trp Ser Leu Ser Leu
            410             415

GGT GGT AAA TAC TTT AAA TTT GGA GAT GCT CAA GCA CAG CTA  1452
Gly Gly Lys Tyr Phe Lys Phe Gly Asp Ala Gln Ala Gln Leu
420             425                     430

CCA ACC AAA GAT AAA GTA GGT AAC TTT GAT AGT AAT GAT GGC  1494
Pro Thr Lys Asp Lys Val Gly Asn Phe Asp Ser Asn Asp Gly
    435             440             445
```

UNITED STATES PATENT AND TRADEMARK OFFICE
CERTIFICATE OF CORRECTION

PATENT NO. : 5,607,846
DATED : March 4, 1997
INVENTOR(S) : Murphy et al.

It is certified that error appears in the above-identified patent and that said Letters Patent is hereby corrected as shown below:

```
TAT GCC TTG GGC GTT AAG CTT GCT TAT CAC GCC AAA TAATCT   1536
Tyr Ala Leu Gly Val Lys Leu Ala Tyr His Ala Lys
        450             455             459
``` col. 31, claim 1, "460" should be --459--

Signed and Sealed this

Seventeenth Day of November, 1998

Attest:

*Attesting Officer*

BRUCE LEHMAN

*Commissioner of Patents and Trademarks*